United States Patent [19]

Barton et al.

[11] Patent Number: 4,590,373
[45] Date of Patent: May 20, 1986

[54] DEVICE FOR MEASUREMENT OF CONTENT OF LOOSE MIXTURES COMPONENTS

[75] Inventors: Piotr Barton, Tychy; Pawel Krzystolik, Pszczyna; Jan Sliz; Roman Dworok, both of Tychy; Kazimierz Lebecki; Ryszard Slotwinski, both of Mikolów, all of Poland

[73] Assignee: Glowny Instytut Gornictwa, Katowice, Poland

[21] Appl. No.: 591,682

[22] Filed: Mar. 21, 1984

[30] Foreign Application Priority Data

Apr. 1, 1983 [PL] Poland ................................. 241369

[51] Int. Cl.$^4$ ............................................. G01N 23/00
[52] U.S. Cl. ................................. 250/308; 250/358.1; 250/505.1
[58] Field of Search ................... 250/308, 358.1, 359.1, 250/505.1, 506.1, 507.1

[56] References Cited

U.S. PATENT DOCUMENTS

| 2,884,539 | 4/1959 | Swift, Jr. ................... 250/358.1 |
| 3,588,507 | 6/1971 | Weinstock et al. ............ 250/308 |
| 4,224,517 | 9/1980 | Lubecki et al. ............... 250/255 |

OTHER PUBLICATIONS

Lovely et al., "The Rapid Assessment of Coal Mine Roadway Dusts Using a Portable Radioactive Device" Australian Symposium, May 1981.
Sacks et al., "Modification of Bureau of Mines BERC Rock Dust Meter", Report of Invest. 8155.

*Primary Examiner*—Janice A. Howell
*Attorney, Agent, or Firm*—Ladas & Parry

[57] ABSTRACT

A device for the measurement of the amounts of components of loose mixtures comprises a beta radiation source, a backscattering detector, a casing integral with a tribranched hollow chamber, divided at its branching point by a beta radiation-permeable membrane, to form a top branch to contain the sample mixture, and bottom branches leading to the detector inlet and source, respectively, and a lid to close the top branch. The lid is linked to the source to place it in an "on" position on closure. The detector feeds via a comparator, an anticoincidence circuit, whose second input is connected to a tuned generator and whose output feeds a reversible counter via a double frequency divider. Instead a frequency divider may follow the comparator. This may be adjustable with a second frequency divider preceding the second input of the anticoincidence circuit.

8 Claims, 5 Drawing Figures

DEVICE FOR MEASUREMENT OF CONTENT OF LOOSE MIXTURES COMPONENTS

BACKGROUND OF THE INVENTION

The invention concerns a device for measurement of loose mixtures components content, particularly for determination of the content of incombustible materials in the dust zones of mine workings and for dust hazards in mines.

Well known is, for instance from Polish description of the applied model No. 27017, a device for determination of solid incombustibles in dust zones, consisting of a beta radiation source and a scintillation probe recording backscattered radiation at the dust sample. Application of the scintillation probe as the radiation detector calls for high voltage supply, which makes intrinsic safety impossible to be guaranteed and eliminates it from its usage underground.

Well known is also, for example from Polish description of the applied model No. 30100, a device serving this purpose, equipped with a semi-conductor detector of backscattered beta radiation at the dust sample. It significantly limits power consumption and enables the application of intrinsically safe electric circuits. However the fact that the radiation source, the sample container and the detector are, as in the previous case, separate elements, exposed to shocks and mutual shifting causes the instability of indications in coal mine conditions.

Similar faults can be found in the solutions well known from foreign literature, for example the Australian device described by C. R. Ailwood, K. Bunch, R. A. Grawitis and I. S. Watt in which a loose mixture sample container and a scintillation probe with a photomultiplier as the detector, constitute a mechanically combined system which does not guarantee stability even at weak shocks. The photomultiplier applied in the probe is very fragile and both the supplying circuit and the current intensity meter are separate instruments joined by cable to the device, which causes difficulties in its use underground. Furthermore, employed in this device is a gamma 238 Pu radiation source with activity 30 m Ci which requires a special type of protective screens. Required sample mass of 25-30 g is very high, too. An American solution PERO has the same faults and disadvantages.

The above described devices for the measurement of content of loose mixtures components, consisting of a radiation source and a scintillation probe or a semi-conductor detector are usually equipped with a battery, a wide-band charge amplifier, an integrator and a indicator. Very long response time and low shock resistance of the indicators are the main faults of such solutions which are particularly inconvenient in coal mine underground conditions.

Well known are also devices for the measurement of content of loose mixtures components equipped instead of the integrator and the indicator with an electronic pulse scaler controlling the digital display by the decoder. These devices have an advantageous, 2.5 times shorter response time than the indicator and furthermore, they are shock-resistant. The main fault of these devices is that they do not indicate directly but they require calibration. There exist a significant difficulty in constructing a device with the direct digital read-out. This difficulty results from the stochastic character of pulse appearance, the mean amount of which at a given time represents the content of the components and from the great amount of surrounding noise, changing accordingly to a given specimen of the detector and the radiation source, a zero level value and transducing sensitivity. These factors cause difficulties in ensuring, from the service point of view, easy calibration of the device to the measurement of dust components content with the direct digital read-out.

SUMMARY OF THE INVENTION

The above mentioned faults and disadvantages are eliminated by using the device for the measurement of content of loose mixtures components as in the invention. According to the invention, the device has an integral casing with a tribranched hollow chamber, divided at the branching point with a beta radiation permeable membrane. This membrane divides the hollow chambers to a top branch, which is the container for the examined loose material sample, with an overleaf closed lid and two bottom branches. One bottom branch leads to a radiation detector and the other bottom branch to a beta radiation source. The radiation source is located in a setting lever device, joined by a transmission to the casing lid, so that the closure of this lid results in setting the source in its "on"-position, while its opening results in setting the source in its "off"- and safe position.

The radiation detector is joined through a comparator, an anticoincidence circuit and a frequency divider to one reversible counter input, the second input of which is joined through this frequency divider and the anticoincidence circuit to a first tuned generator. In a second embodiment according to the invention, the radiation detector is joined through the comparator, the frequency divider and the anticoincidence circuit to one reversible counter output. In the latter case, the second reversible counter input is joined to the first tuned generator only through the anticoincidence circuit. In a third embodiment of the device according to the present invention, the radiation detector is joined through the comparator, the adjustable frequency divider and the anticoincidence circuit to one reversible counter input. In this version the second reversible counter input is joined through the anticoincidence circuit to the second adjustable frequency divider, the input of which is joined to the second generator output, which in this case does not have to be tuned. Thus, the third version of the device according to the present invention differs from the second version in that, instead of the first frequency divider there is the first adjustable frequency divider, and instead of the first tuned generator, there is the second adjustable frequency divider. In all versions, the reversible counter outputs are attached through a decoder to digital display inputs and a gating anticoincidence circuit input is joined to one control system the output of which is joined to the second tuned generator. The turn-off output of the control system is joined together with an unstable immobilizing change-over switch to the turn-off system input, the output of which is joined to a relay coil, equipped with a contact system and located between one terminal of a battery and the supply terminals of the device functional systems. The control system has an additional output of preliminary setting to zero, attached to the reversible counter and an additional output attached to the gating input of the digital display and also it has an additional input joined to a stable change-over switch, changing the measurement cycle time during calibration and measurement.

The device according to the invention ensures the stability of mutual position of the radiation source, the detector and the loose mixture sample and its small overall dimensions and at the same time short distance among these elements makes possible the reduction of the required sample mass below 20 g and application of the radiation surce with activity not exceeding 5 m Ci 185 MBq. Furthermore, proper coupling of the device casing lid with the source setting lever ensures significant reduction of the radiation dose absorbed by an operator. An important advantage of the device according to the invention is the direct digital read-out of the percentage content of loose mixtures components and high supplying autonomy of the device and at the same time possibly low electric power consumption at one measurement. The above mentioned features and advantages make the device especially useful for measurements of the content of incombustible materials in dust zones with calcareous and other incombustible dusts, for mine working protection against coal dust explosion.

DESCRIPTION OF THE PREFERRED EMBODIMENT

Figure 1:
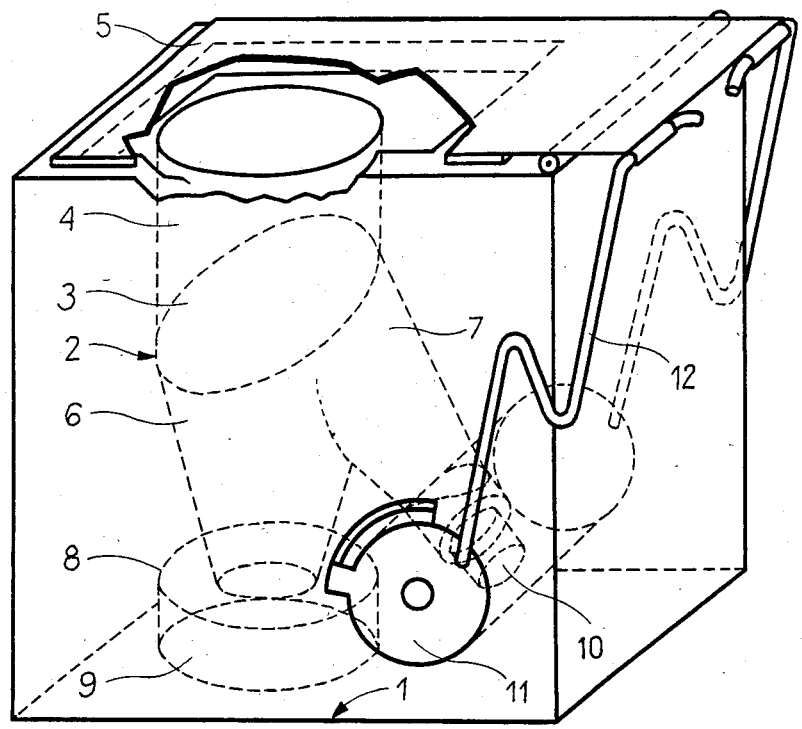
FIG. 1 shows the device integral casing during measurement.

Referring to FIG. 1, a device for the measurement of content of loose matter components has an intergral casing 1 with tri-branched hollow chamber 2, divided at the branching point with a beta radiation permeable membrane 3. This membrane 3 divides the hollow chamber 2 to a top branch 4, which is the container for the examined loose material sample and an overleaf closed lid 5 and also to two bottom branches 6 and 7. One bottom branch 6 leads to the inlet 8 of a radiation detector 9, and the other bottom branch 7 to a beta radiation source 10. The radiation source 10 is located in a regulating unit 11 joined through a transmission 12 to the casing 1 lid 5, so that the closure of this lid 5 results in setting the source in its "on"-position, while its opening results in setting the source in its "off"- and safe position.

Figure 3:
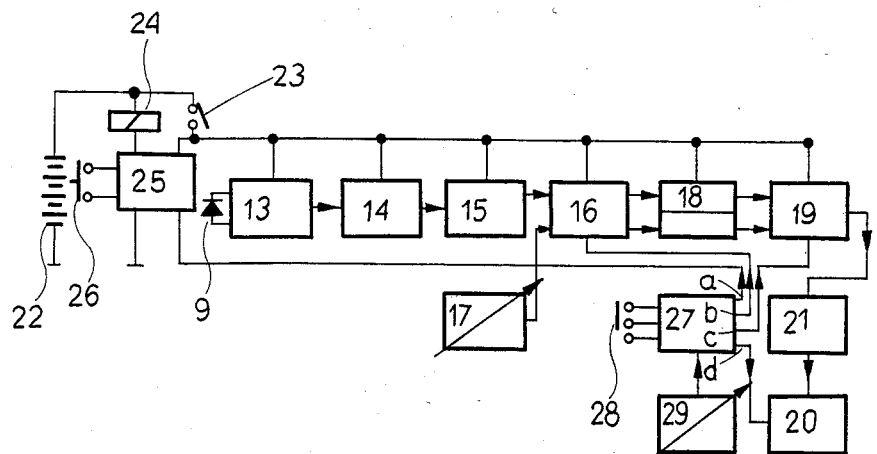
FIG. 3 is a diagram of one form of the electronic system of the device
Figure 4:
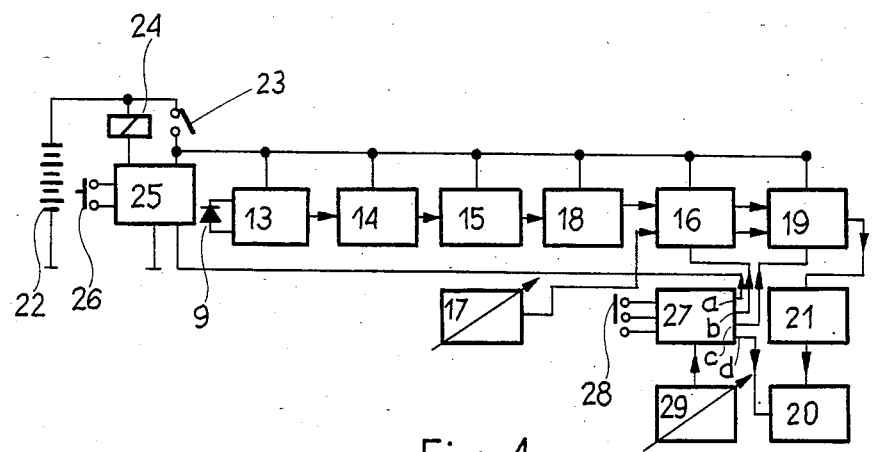
FIG. 4 is a second form of the electronic system.

Semiconducting detector 9 is joined to an amplifier 13 input, the output of which is joined to a d.c. restorer 14 input. D.C. restorer 14 output is joined to a comparator 15 input, the output of which controls one anticoincidence circuit 16 input. The second anticoincidence circuit 16 input is joined to the output of a first tuned generator 17. Both outputs of the anticoincidence circuit 16 are joined to the inputs of a double frequency divider 18, both outputs of which are attached to positive and negative reversible counter 19 outputs. The reversible counter 19 is joined to a digital display 20 through the decoder 21. The contact system 23 of relay 24 is connected in series between one terminal of battery 22 and the supply terminals of the device functional systems. Relay 24 coil is joined by one end to the battery 22 and by the other to the turn-off system 25 outputs, the inputs of which are attached to contact systems of an unstable immobilizing change-over switch 26 and also turn-off output a of a control system 27. The contact system of a stable change-over switch 28 and the output of a second tuned generator 29 are attached to the control system inputs. Output b the control system 27 is attached to the gating anticoincidence circuit 16 input. Additional output of the preliminary setting to zero c of the control system 27 is joined to the setting to zero input of the reversible counter 19. Another additional reversible counter 27 output d is attached to the gating input of the digital display 20. The device, according to the invention shown in FIG. 4 of the drawing, has the frequency divider 18 joined between the comparator 15 and the anticoincidence circuit 16 both outputs of which are directly attached to both reversible counter 19 inputs. The anticoincidence circuit 16 is equipped with an integral generator with a constant frequency. In the actual circuit as shown in FIG. 4, the frequency divider 18 can be made up from an integrated counter. In the actual circuit in FIG. 3, a frequency divider 28 can be made up from two independent integrated counters or one integrated reversible counter, the positive input of which is joined through the anticoincidence circuit 16 to the comparator 15 output, the negative input is joined through the anticoincidence circuit 16 to the first tuned generator 17, the positive transfer output is joined to the positive reversible counter 19 output, and finally the negative transfer output is joined to the negative reversible counter 19 input. In the third embodiment of the device shown in FIG. 5, the frequency divider 18, is an adjustable divider connected between the comparator 15 and the anticoincidence circuit 16. In this version the first tuned generator 17 is replaced by a second adjustable frequency divider 30 connected between the anticoincidence circuit 16 and a second generator 29, which in this case does not have to be tuned.

The device according to the present invention shown in its first embodiment in FIGS. 1, 2 and 3 of the drawing, works in the following way. Dust sample material is placed in the container having the form of the top branch 4 of the hollow chamber 2 in the integral casing 1. After lid closing, the radiation source 10 turns to the working position and the beta radiation beam directed to the dust sample and after backscattering it is recorded by the semiconducting radiation detector 9 which generates electric pulses under the influence of the radiation. After pressing the button of the unstable immobilizing change-over switch 26 located outside the casing, the turn-off system 25 prompts current flow through the relay 24 coil, the contact system 23 of which passes the battery 22 voltage onto the ends of supply terminals of the device functional system. As a result of the self-sustaining operation of the turn-off system 25, the relay 24 remains in an excited state even after releasing the button of the unstable immobilizing change-over switch 26. Detector 9 pulses are amplified in the wide-band amplifier 13 and they pass to the inlet of the d.c. restoration system 14. Because of the capacitive coupling in the amplifier 13 without the d.c. restoration system 14, the pulse level would drop with the frequency increase. The comparator 15 acts as the pulse selector, eliminating pulses with too low amplitude, it forms them and next passes these pulses through the anticoincidence circuit 16 and through the double frequency divider 18 to the positive reversible counter 19 output. The pulse from the first tuned generator is also supplied through the anticoincidence circuit 16 and the double frequency divider 18 to the negative reversible counter input. The frequency divider 18 lowers frequency of both signals in the same constant ratio. The anticoincidence circuit 16 has the third generator with constant frequency much higher than the frequency at the comparator 15 output and that of the first tuned generator 17. In each first half-cycle of the third generator oscillation, the simultaneous pulse occurance at the comparator 15 output and the first tuned generator 17 is checked. If this simultaneous pulse condition does not occur, they are passed without any changes to the frequency divider 18. If the simultaneous pulse condition exits then the pulse from the comparator 15 is passed to the frequency divider 18 input, while the pulse of the first tuned generator 17 is recorded and passed to the second frequency divider 18 input substantially without delay in the second half-cycle of the third generator oscillation. The reversible counter 19 separates the pulses from the first tuned generator 17 from the pulses coming from the comparator 15. Before counting, the reversible counter 19 is each time reduced to zero by the pulse occuring at the preliminary setting to zero c output of the control system 27. Pulse counting lasts as long as there is a signal at the control system 27 output b. Counting time is inversely proportional to the frequency of the second tuned generator 29. After signal disappearance at the control system 27 output c, the anticoincidence system 16 is blocked and the reversible counter 19 stops pulse counting. Then appears a signal at the control system 27 output d, which unblocks the digital display 20. The digital display 20 controlled by the decoder 21 of the reversible counter 19 shows for several minutes a result of the measurement. The measurement result R is expressed by the dependents presented in equation 1:

$$R = \frac{f - f_1}{n} \cdot \frac{A}{f_2} \qquad (1)$$

where:
f—frequency of comparator 15
$f_1$—frequency of the first tuned generator 17
$f_2$—frequency of the second tuned generator 29
n—multiplication factor of the frequency divider 18
A—constant of the control system 27

After displaying the measurement results, there occurs a command signal of the turn-off system 25 at the turn-off output a of the control system 27, which results in the opening of the relay 24 of contact system 23 and thus, in switching the whole system off from the supplying voltage. The stable change-over switch 28 has two positions: "calibration" and "measurement". "Calibration" position allows adjustment to zero and provides sensitivity control. After pressing the button of the unstable immobilizing change-over switch 26, the control system 27 provides the automatic taking of the next 9 successive measurements in a shortened measurement time and with measurement accuracy reduced by one decimal place. It also provides taking of decimal measurements during the full duration time with complete accuracy, and then the device switches off. Scale regulation and shifting is responsive to the frequency change of the first tuned generator 17 and scale sloping regulation is responsive to the frequency change of the second tuned generator 29.

Figure 2:
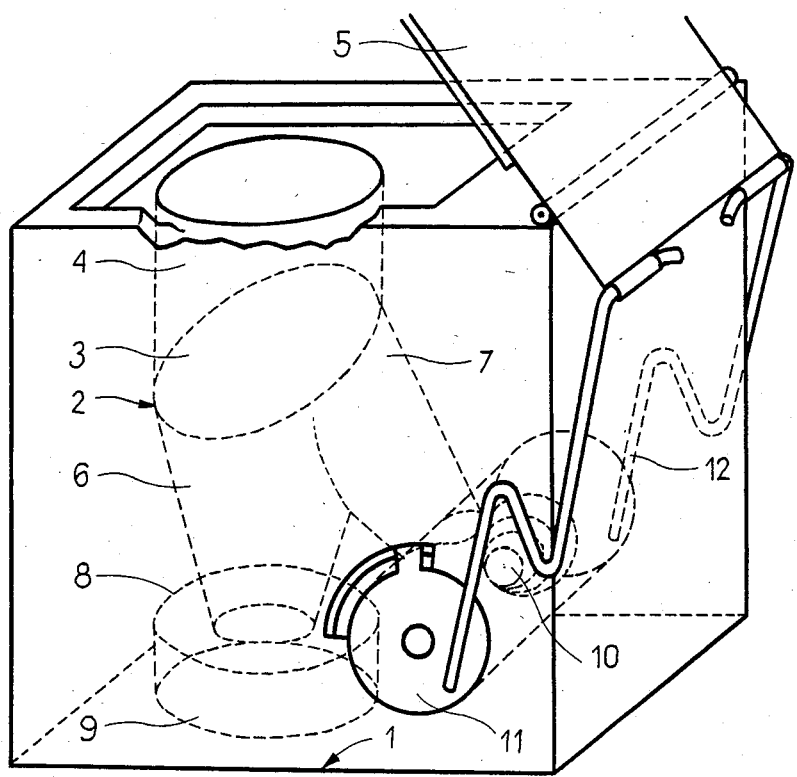
FIG. 2 shows the casing before taking measurements.

The operation of the device according to the present invention in its second embodiment as in the FIGS. 1, 2 and 4 of the drawing is nearly completely identical but the frequency of the first tuned generator 17 is then reduced. The measurement result R is expressed in this case by the dependents presented in equation 2:

$$R = \frac{f}{n} - f_1 \cdot \frac{A}{f_2} \qquad (2)$$

The advantage of this solution is certain simplification in the structure which however increases the sensitivity of the measurement accuracy to the frequency stability of the first tuned generator 17.

Figure 5:
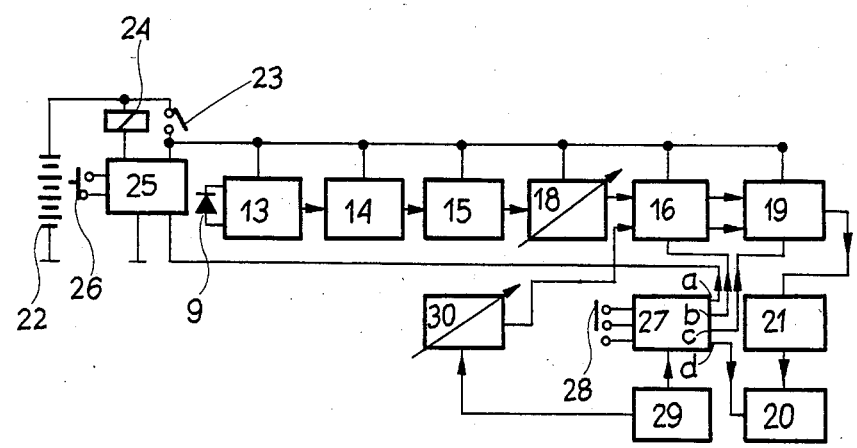
FIG. 5 is a third form of the electronic system.

Operation of the device according to the present invention in its third embodiment shown, presented in FIGS. 1,2 and 5 of the drawing is nearly completely identical, but the measurement result R is defined by the dependents of equation 3:

$$R = \left(\frac{f}{n_1} - \frac{f_2}{n_2}\right) \frac{A}{f_2} \qquad (3)$$

where:
$n_1$—multiplication factor of the frequency divider 18 as adjusted
$n_2$—multiplication factor of the frequency divider 30 as adjusted.

The advantge of this solution is improved performance using integrated circuits having CMOS components and also the possibility of utilizing a generator 29 which is more time- and temperature-stable and which in the third embodiment does not have to be tuned.

We claim:

1. A device for measurement of the content of loose mixtures components, comprising a beta radiation source, a detector recording radiation backscattering from said radiation source at a mixture sample, a casing integral with a tribranched hollow chamber mounted therein, the chamber being divided at a branching point by a beta radiation-permeable membrane, to form a top branch which defines a container for a loose material sample to be examined, and two bottom branches, one of which leads to an inlet for said radiation detector, and the other of which leads to said radiation source, and a movable lid connected to means for selectively closing the container defined by said top branch.

2. A device according to claim 1, wherein said means includes a movable member in which said radiation source is located, said means being drivingly connected to said lid so that closure of said lid results in movement of said movable member to place the radiation source in an "on" position, whereas opening of the lid results in movement of the member to place the radiation source in an "off" position in which access can safely be gained to the container.

3. A device according to claim 1, wherein said radiation detector is connected by way of a comparator, an anticoincidence circuit and a frequency divider to a first input of a reversible counter, a second input of said reversible counter being connected to a tuned generator by means of said frequency divider and said anticoincidence circuit.

4. A device according to claim 1, wherein said radiation detector is connected by way of a comparator, a frequency divider and an anticoincident circuit to a first input of a reversible counter, a second input of the reversible counter being connected to a tuned generator by means of said anticoincidence circuit.

5. A device according to claim 1, wherein said radiation detector is connected by way of a comparator, an adjustable frequency divider and an anticoincidence circuit to a first input of a reversible counter, a second input of said reversible counter being connected to the output of a second frequency divider by way of said anticoincidence circuit.

6. A device according to claim 3, 4 or 5, wherein said reversible counter has its output connected by way of a decoder to the inputs of a digital display, and wherein the gating input of the anticoincidence circuit is connected to one output of a second tuned generator.

7. A device according to claim 6, including a control system having a turn-off output connected, together with an unstable immobilizing change-over switch, to a switching-off system, said switching-off system having an output which is combined with a relay coil for driving switching contacts located between one terminal of a battery and the supply terminals of the functional system of the device.

8. A device according to claim 7, wherein said control system further includes an output for preliminary setting to zero, a zero-adjustable output connected to the gating input of a digital display, and an additional input joined to a stable change-over switch for changing the measurement cycle time during calibration and measurement.

* * * * *